United States Patent
Hanner et al.

(10) Patent No.: US 10,149,937 B2
(45) Date of Patent: *Dec. 11, 2018

(54) INFUSION ADAPTER FOR DRUG TRANSFER ASSEMBLY

(71) Applicant: Becton Dickinson and Company Limited, Dun Laoghaire (IE)

(72) Inventors: Gert Hanner, Mjohult (SE); Fredrik Stoltz, Veberöd (SE); Alpa Patel, Metuchen, NJ (US); Weston F. Harding, Lehi, UT (US); Paul Fearis, Reisterstown, MD (US)

(73) Assignee: Becton Dickinson and Company Limited, Dun Laoghaire (IE)

( * ) Notice: Subject to any disclaimer, the term of this patent is extended or adjusted under 35 U.S.C. 154(b) by 9 days.

This patent is subject to a terminal disclaimer.

(21) Appl. No.: 15/375,949

(22) Filed: Dec. 12, 2016

(65) Prior Publication Data

US 2017/0087297 A1  Mar. 30, 2017

Related U.S. Application Data

(63) Continuation of application No. 14/091,506, filed on Nov. 27, 2013, now Pat. No. 9,550,024.

(60) Provisional application No. 61/731,902, filed on Nov. 30, 2012.

(51) Int. Cl.
*A61M 5/162* (2006.01)
*A61M 5/14* (2006.01)
*A61M 39/10* (2006.01)

(52) U.S. Cl.
CPC .......... *A61M 5/162* (2013.01); *A61M 5/1407* (2013.01); *A61M 2039/1077* (2013.01); *Y10T 137/9029* (2015.04)

(58) Field of Classification Search
CPC ................ A61M 5/162; A61M 39/221; A61M 2039/1033; A61M 39/1011; A61M 2039/1077
See application file for complete search history.

(56) References Cited

U.S. PATENT DOCUMENTS

| 3,755,697 A | 8/1973 | Miller |
| 3,822,700 A | 7/1974 | Pennington |
| 4,851,006 A | 7/1989 | Tuke |
| 8,075,550 B2 | 12/2011 | Nord et al. |
| 2003/0191445 A1 | 10/2003 | Wallen et al. |

(Continued)

FOREIGN PATENT DOCUMENTS

| JP | 2005537048 A | 12/2005 |
| JP | 2007236438 A | 9/2007 |
| WO | 2010069361 A1 | 6/2010 |

*Primary Examiner* — Bradley J Osinski
*Assistant Examiner* — Nilay Shah
(74) *Attorney, Agent, or Firm* — The Webb Law Firm

(57) ABSTRACT

An infusion adapter for connection with an infusion fluid container includes a connection portion including an anchor component for connecting to an injection port of the infusion fluid container, and a first port adapted for connection with a syringe assembly containing a medication fluid. The first port is in fluid communication with the connection portion. The anchor component is configured to securely connect the infusion adapter to the infusion fluid container to substantially prevent disconnection of the infusion adapter from the infusion fluid container once the infusion adapter is connected to the infusion fluid container.

9 Claims, 13 Drawing Sheets

(56) References Cited

U.S. PATENT DOCUMENTS

2005/0182383 A1 8/2005 Wallen
2005/0215976 A1 9/2005 Wallen

INFUSION ADAPTER FOR DRUG TRANSFER ASSEMBLY

CROSS-REFERENCE TO RELATED APPLICATION

This application is a continuation application of U.S. application Ser. No. 14/091,506, filed Nov. 27, 2013, which claims priority to U.S. Provisional Application Ser. No. 61/731,902, filed Nov. 30, 2012, which is hereby incorporated by reference in its entirety.

BACKGROUND OF THE INVENTION

1. Field of the Disclosure

The present disclosure relates generally to a drug transfer assembly. More particularly, the present disclosure relates to an anchor component for securely connecting an infusion adapter to an intravenous bag for a drug transfer procedure.

2. Description of the Related Art

Intravenous therapy applications allow patients to receive infusion and medication treatment. For example, therapy may include the administration of medications by IV using intravenous and subcutaneous or hypodermis routes, i.e., into the bloodstream and under the skin. Examples of medical treatments that intravenous therapy applications may provide to a patient include antibiotics, pain management medications, cancer treatments, and similar medications.

Medications may be packaged as "pre-filled" devices, wherein a syringe assembly is pre-filled with medication prior to being packaged and delivered to a patient. "Pre-filled" devices eliminate the need for a user to fill the device prior to injection.

Certain drugs or medications are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. In addition, drugs may be provided as multipart systems that require mixing prior to administration. For example, one or more liquid components, such as flowable slurries, and one or more dry components, such as powdered or granular components, may be provided in separate containers that require mixing prior to administration.

A patient may be provided with an intravenous system that includes intravenous tubing and a connector that is adapted to receive an injector and/or syringe assembly containing a required medication. In this manner, when a treatment is needed, a patient or a medical practitioner is able to connect a syringe assembly to the connector and then inject a medication intravenously into the patient via the injector and/or syringe assembly, the connector, and the intravenous tubing.

When performing infusion, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question. However, it has been found that an unsecure connection between the syringe and the injection port of the infusion bag may cause problems such as accidental or inadvertent disconnection of the syringe from the infusion bag, pollution of the working environment because of leakage, and high forces required to pierce a fluid barrier of the injection port of the infusion bag.

SUMMARY OF THE INVENTION

In one embodiment, an infusion adapter for connection with an infusion fluid container includes a connection portion including an anchor component for connecting to an injection port of the infusion fluid container, and a first port adapted for connection with a syringe assembly containing a medication fluid. The first port is in fluid communication with the connection portion. The anchor component is configured to securely connect the infusion adapter to the infusion fluid container to substantially prevent disconnection of the infusion adapter from the infusion fluid container once the infusion adapter is connected to the infusion fluid container.

The infusion adapter may further include a second port adapted for connection with an intravenous line adapted for connection to a bloodstream of a patient with the second port in fluid communication with the connection portion. The anchor component may be a helical thread. The helical thread may extend about an entire length of the connection portion. The helical thread may only extend one revolution circumferentially around the connection portion. The anchor component may reduce a force required by a user to pierce a fluid barrier member of the injection port of the infusion fluid container. The connection portion may define first and second fluid channels with the first channel in fluid communication with the first port and the second channel in fluid communication with the second port. The connection portion may be a spike having a puncturing point. The helical thread may be configured to self-tap a corresponding thread within a portion of the infusion fluid container when the connection portion is received by the infusion fluid container.

In another embodiment, an adapter for connection with a container includes a connection portion configured to be connected to a first container with the connection portion including a helical thread. The adapter further includes at least one port adapted to be connected to a second container with the connection portion configured to be in fluid communication with the at least one port. The connection portion and the helical thread are configured to be received by a portion of the first container with the helical thread configured to securely connect the connection portion to the first container once the connection portion is connected to the first container.

The helical thread may extend about an entire length of the connection portion. The helical thread may only extend one revolution circumferentially around the connection portion. The helical thread may reduce a force required by a user to pierce a fluid barrier member of the first container. The at least one port may include first and second ports with the first port configured to be connected with the second container and the second port configured to be connected with a third container. The connection portion may define first and second fluid channels with the first channel in fluid communication with the first port and the second channel in fluid communication with the second port. The connection portion may be a spike having a puncturing point. The helical thread may be configured to self-tap a corresponding thread within a portion of the first container when the connection portion is received by the first container.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
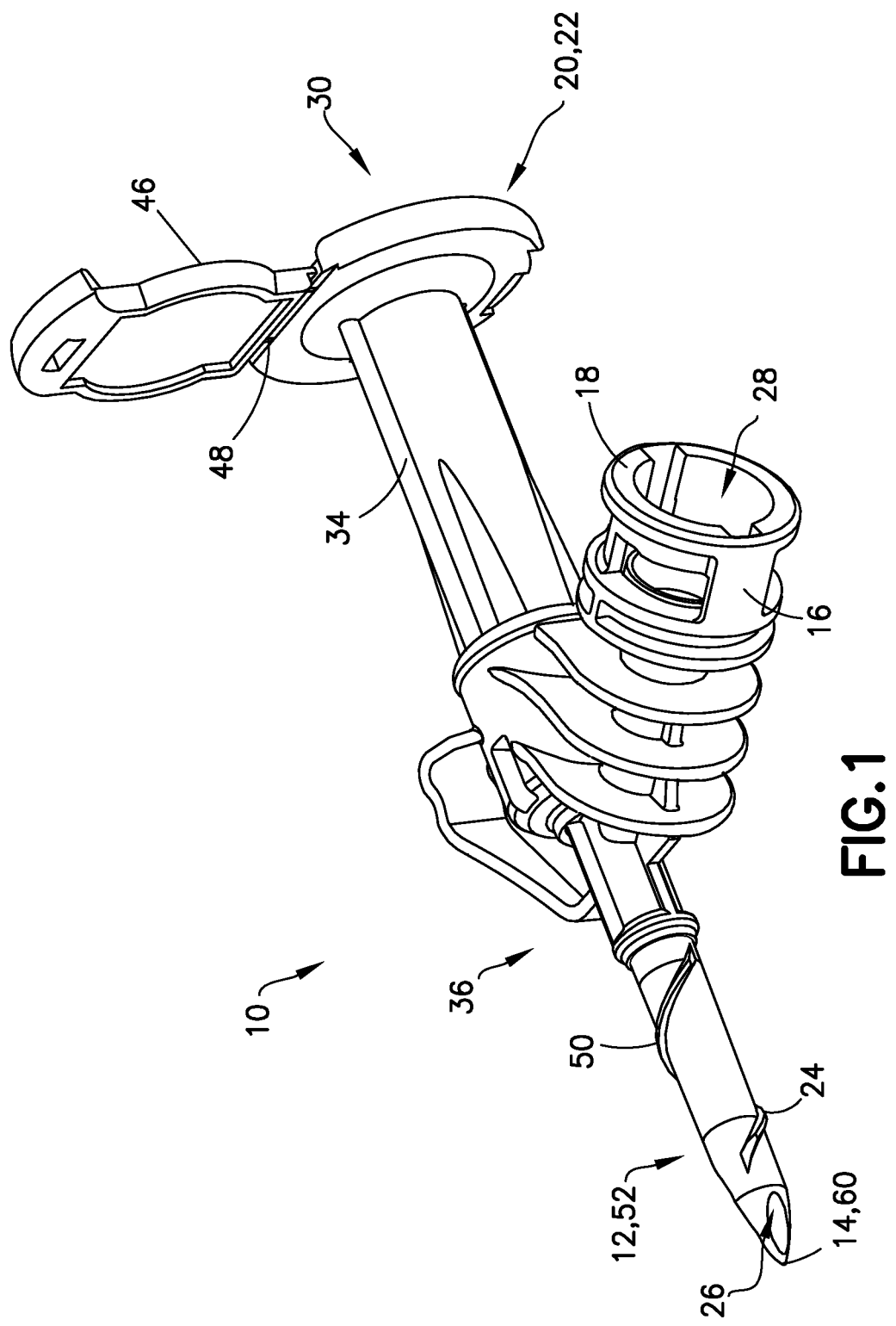
FIG. 1 is a perspective view of an infusion adapter in accordance with an embodiment of the present invention.
Figure 2:
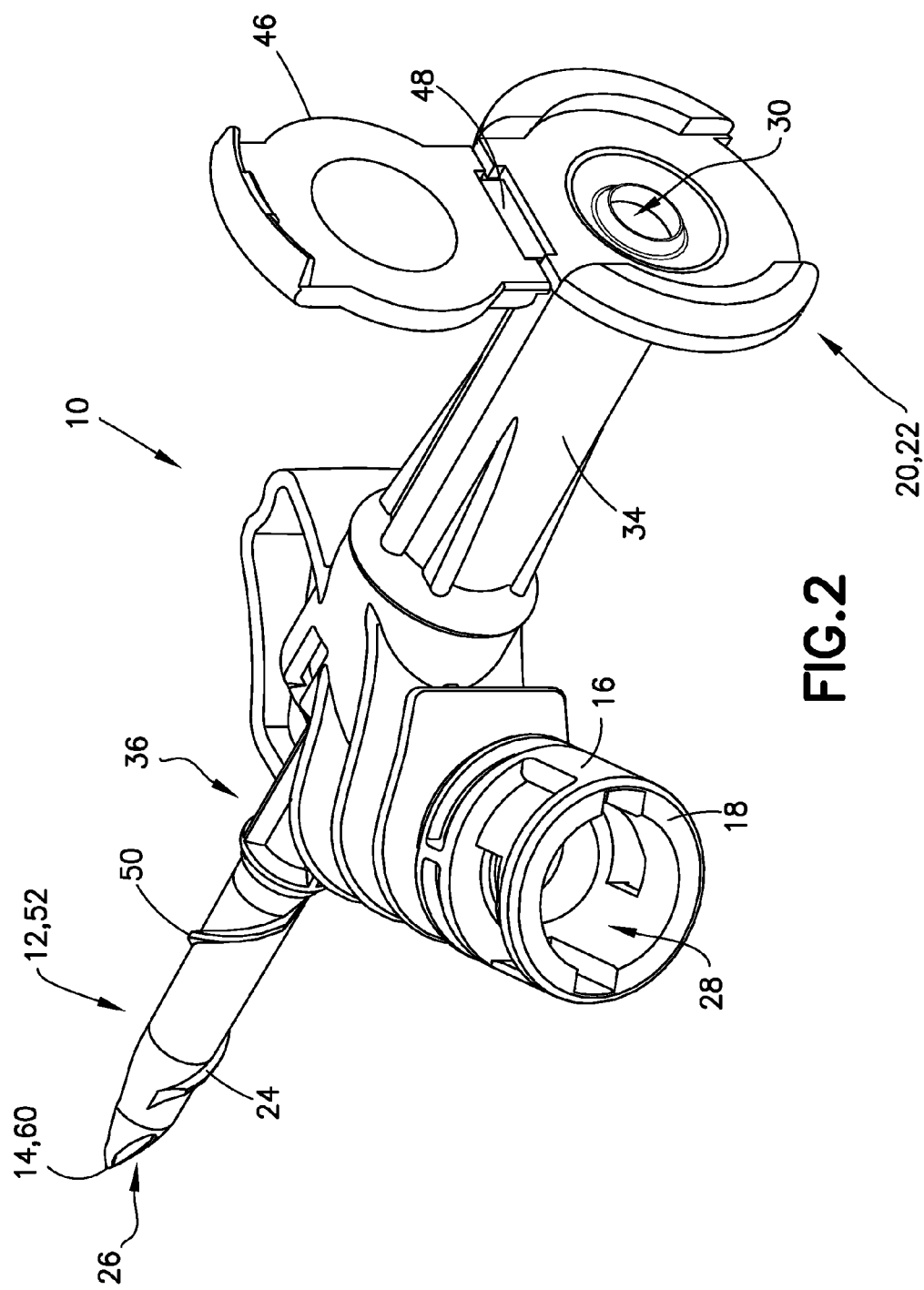
FIG. 2 is another perspective view of the infusion adapter of FIG. 1 in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Referring to FIGS. 1-13, an infusion adapter 10 includes a connection portion 12 located at a first end 14, a first port 16 located at a first port end 18, and a second port 20 located at a second port end 22. Connection portion 12 includes an anchor component 24 and a fluid channel 26 and a fluid channel 32, although only a single channel arrangement may also be utilized. First port 16 includes a first port fluid channel 28 and second port 20 includes a second port fluid channel 30. As shown more clearly in FIGS. 12 and 13, the fluid channel 26 of connection portion 12 is in fluid communication with first port fluid channel 28 of first port 16 such that a fluid may flow into infusion adapter 10 at first port 16, travel through first port fluid channel 28 to fluid channel 26 of connection portion 12 and out first end 14 of infusion adapter 10. The fluid channel 32 of connection portion 12 is in fluid communication with second port fluid channel 30 of second port 20 such that a fluid may flow into infusion adapter 10 at first end 14 of connection portion 12, travel through fluid channel 32 to second port fluid channel 30 and out second port 20 of infusion adapter 10.

Referring to FIGS. 1-13, in one embodiment, infusion adapter 10 may comprise a generally Y-shape. Further, it is contemplated that infusion adapter 10 may be made available in a variety of shapes and sizes as long as first port 16 is spaced a distance from second port 20 so that first port 16 may be connected to a syringe assembly containing a medication fluid and second port 20 may be connected to an intravenous line that is adapted for connection to a bloodstream of a patient as will be described in more detail below. For example, in another embodiment, infusion adapter 10 may comprise a generally T-shape.

Figure 3:
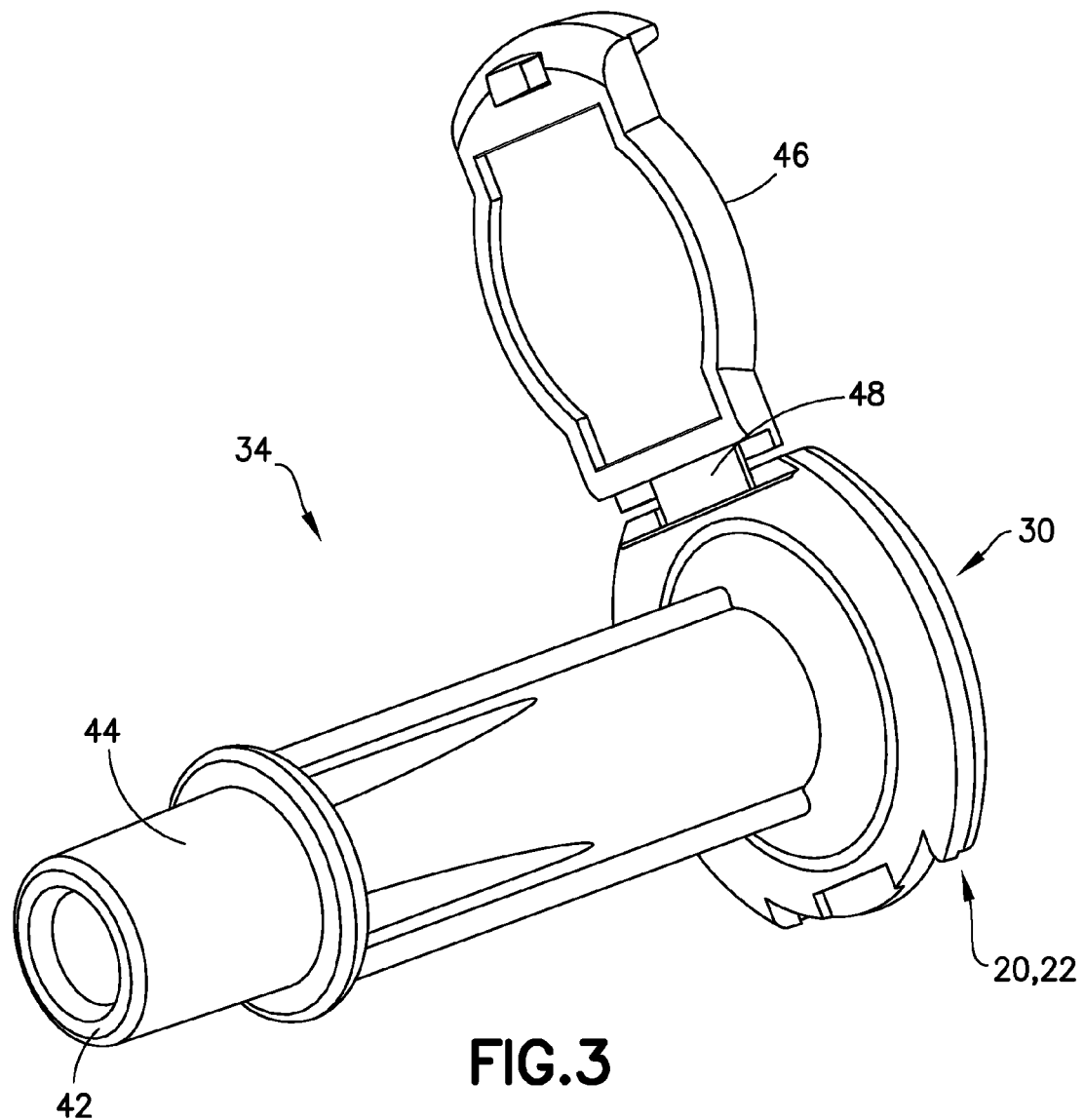
FIG. 3 is a perspective view of an intravenous line connector of the infusion adapter of FIG. 1 in accordance with an embodiment of the present invention.
Figure 4:
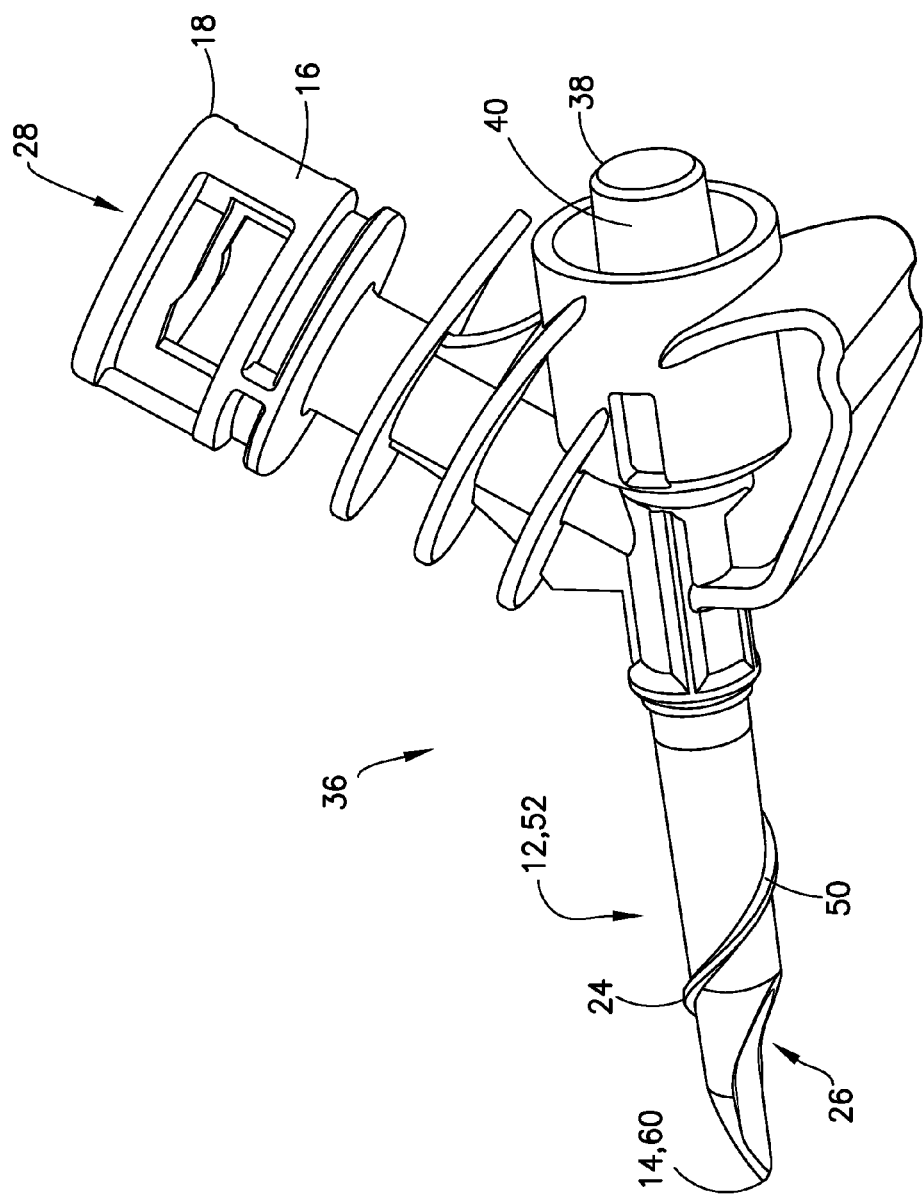
FIG. 4 is a perspective view of a main body of the infusion adapter of FIG. 1 with the intravenous line connector of FIG. 3 removed in accordance with an embodiment of the present invention.
Figure 5:
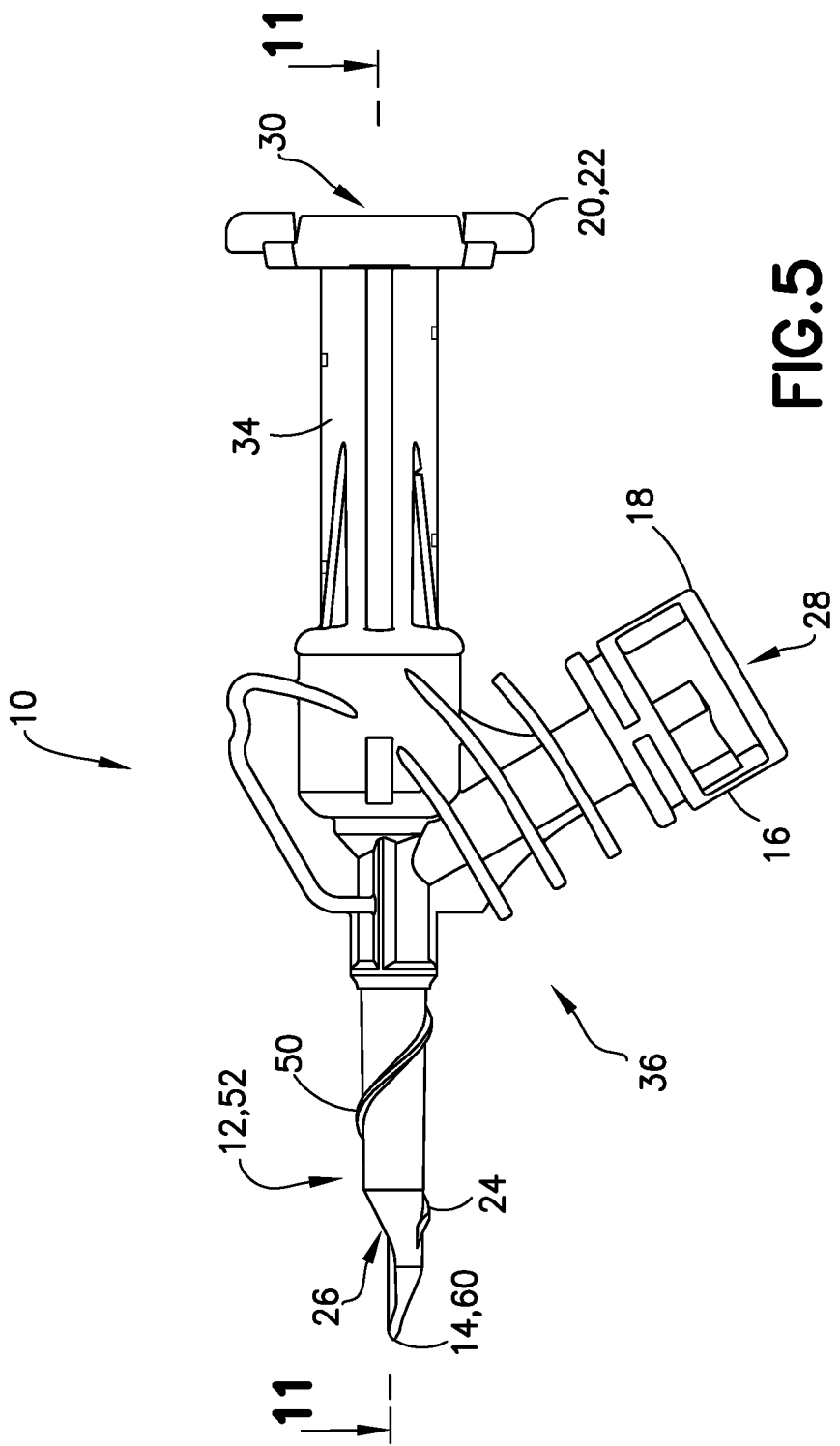
FIG. 5 is a side view of the infusion adapter of FIG. 1 in accordance with an embodiment of the present invention.
Figure 6:
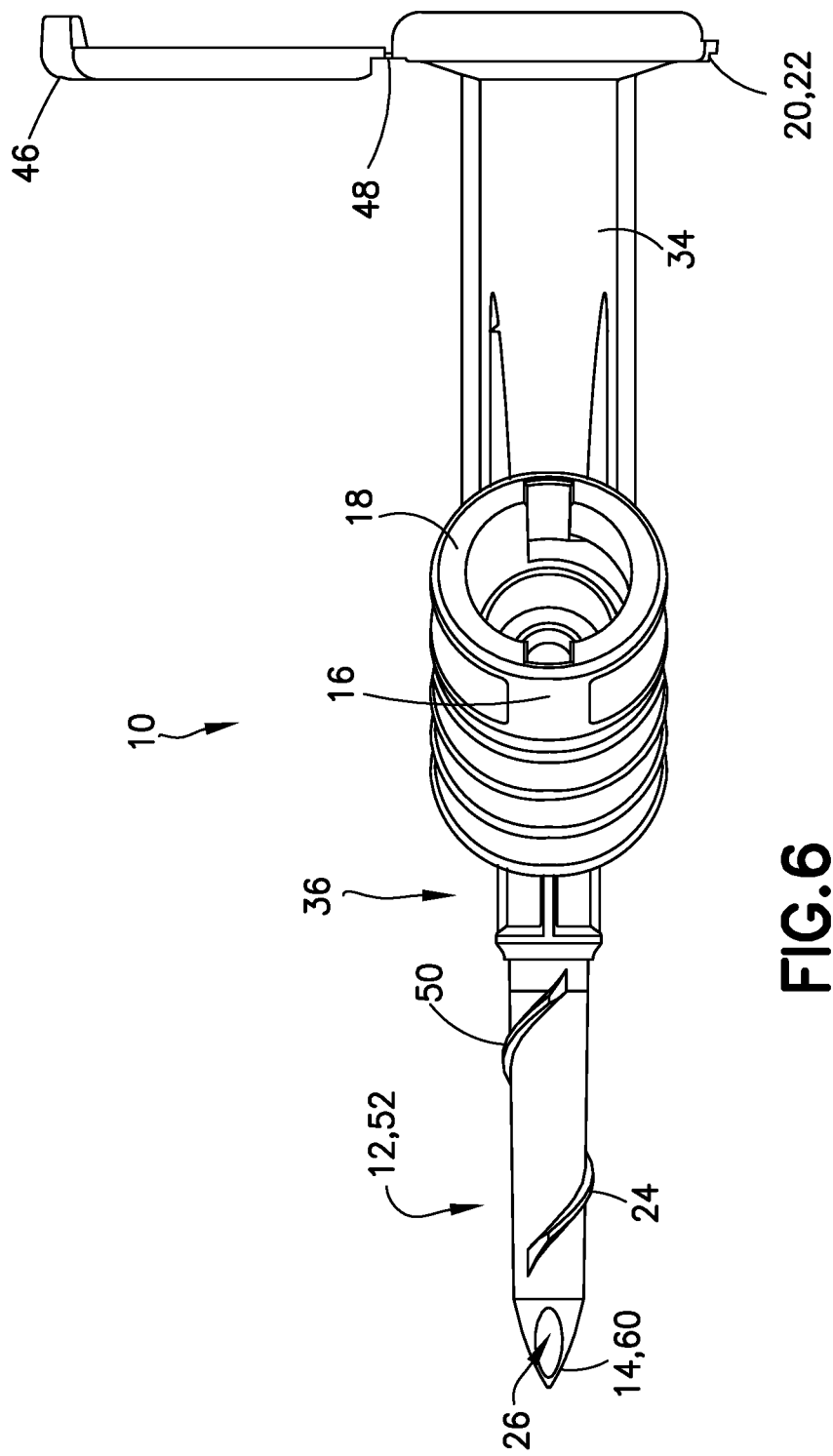
FIG. 6 is a top view of the infusion adapter of FIG. 1 in accordance with an embodiment of the present invention.
Figure 7:
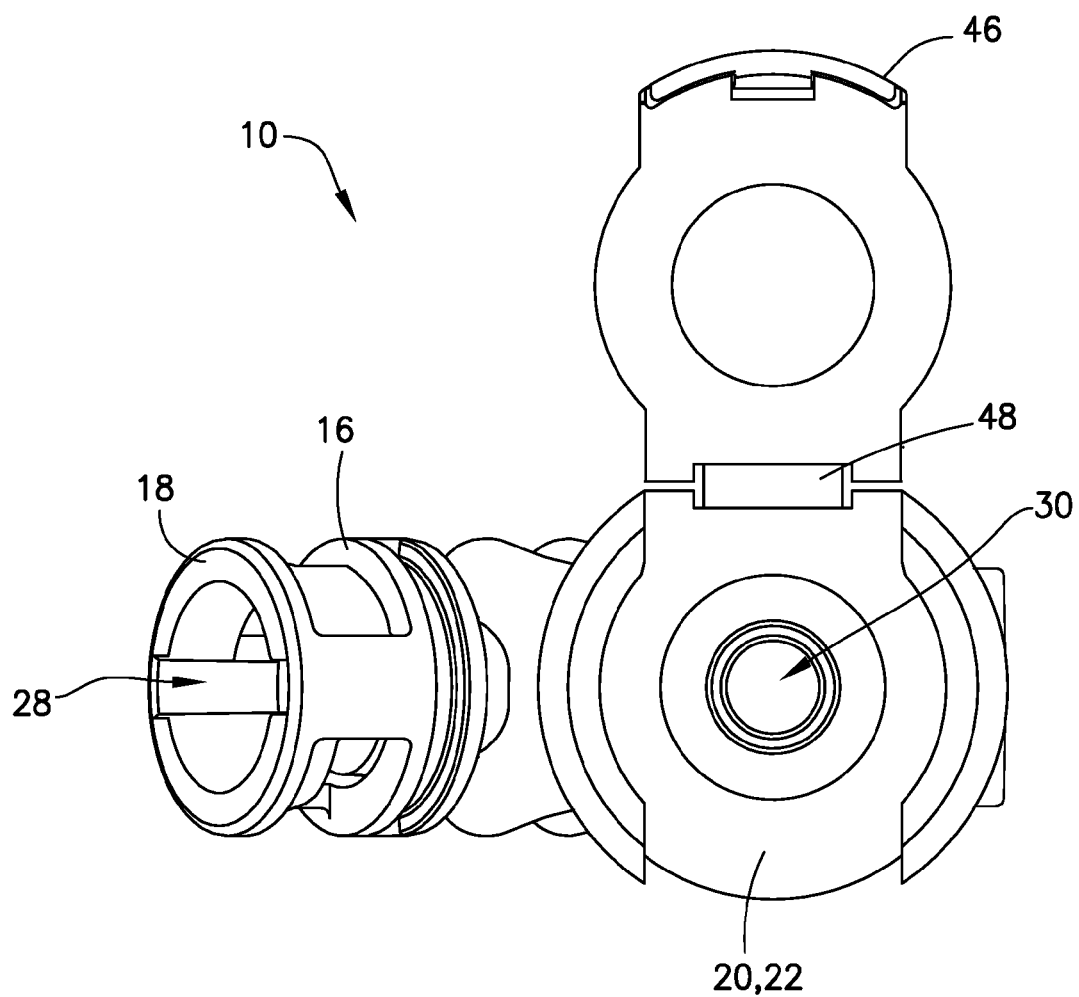
FIG. 7 is a rear view of the infusion adapter of FIG. 1 in accordance with an embodiment of the present invention.
Figure 8:
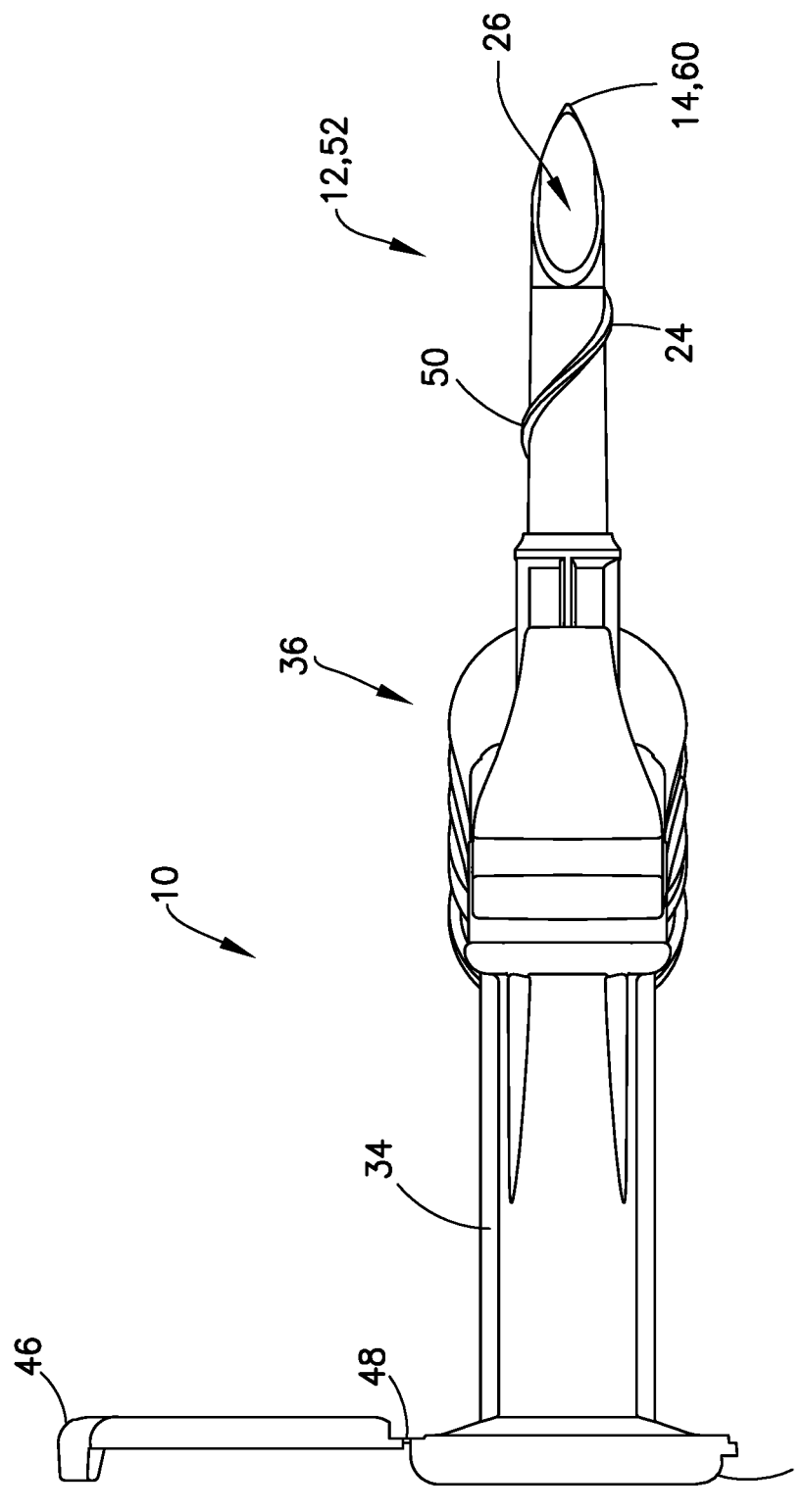
FIG. 8 is a bottom view of the infusion adapter of FIG. 1 in accordance with an embodiment of the present invention.
Figure 9:
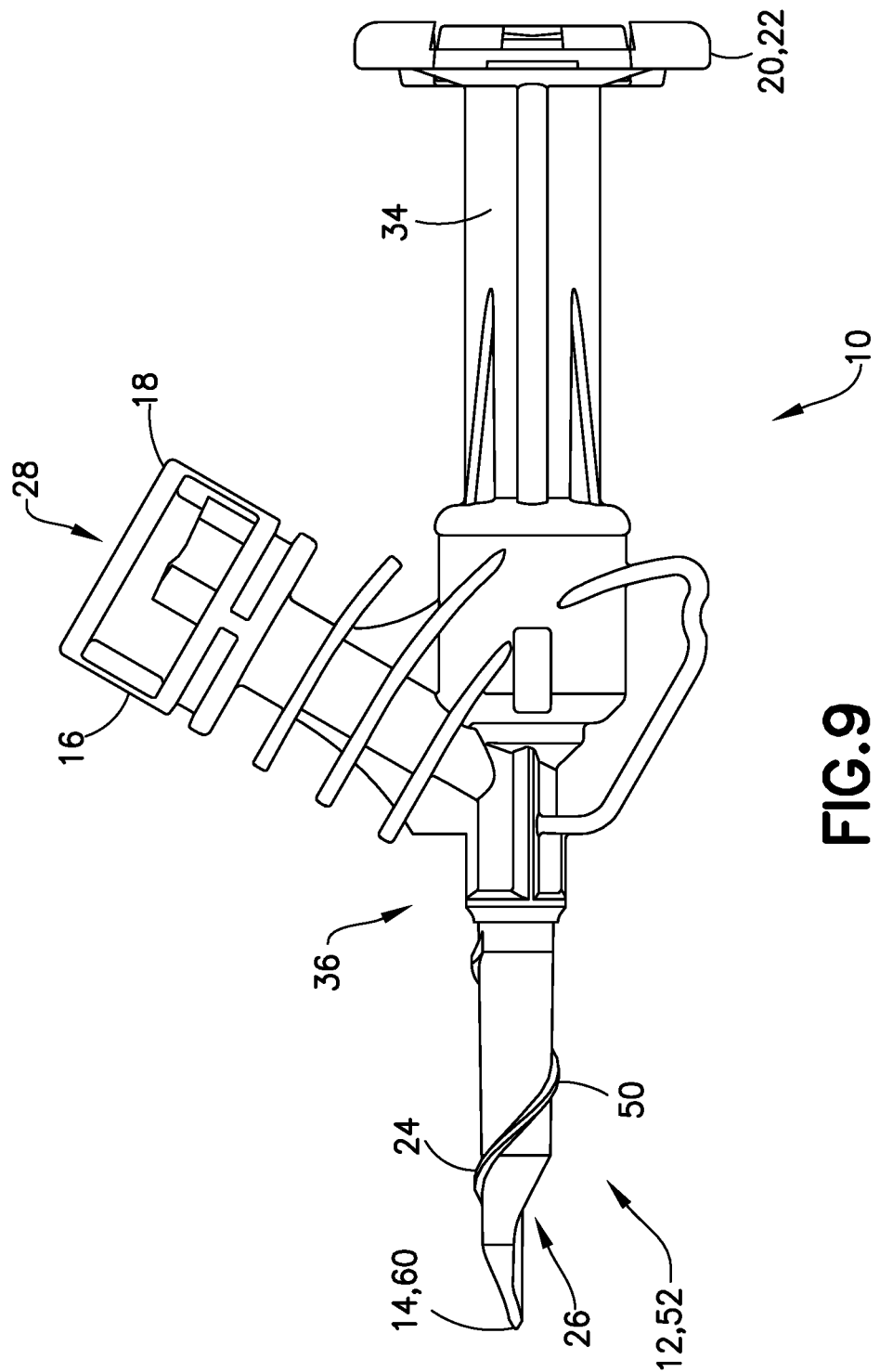
FIG. 9 is a side view of the infusion adapter of FIG. 1 in accordance with an embodiment of the present invention.
Figure 10:
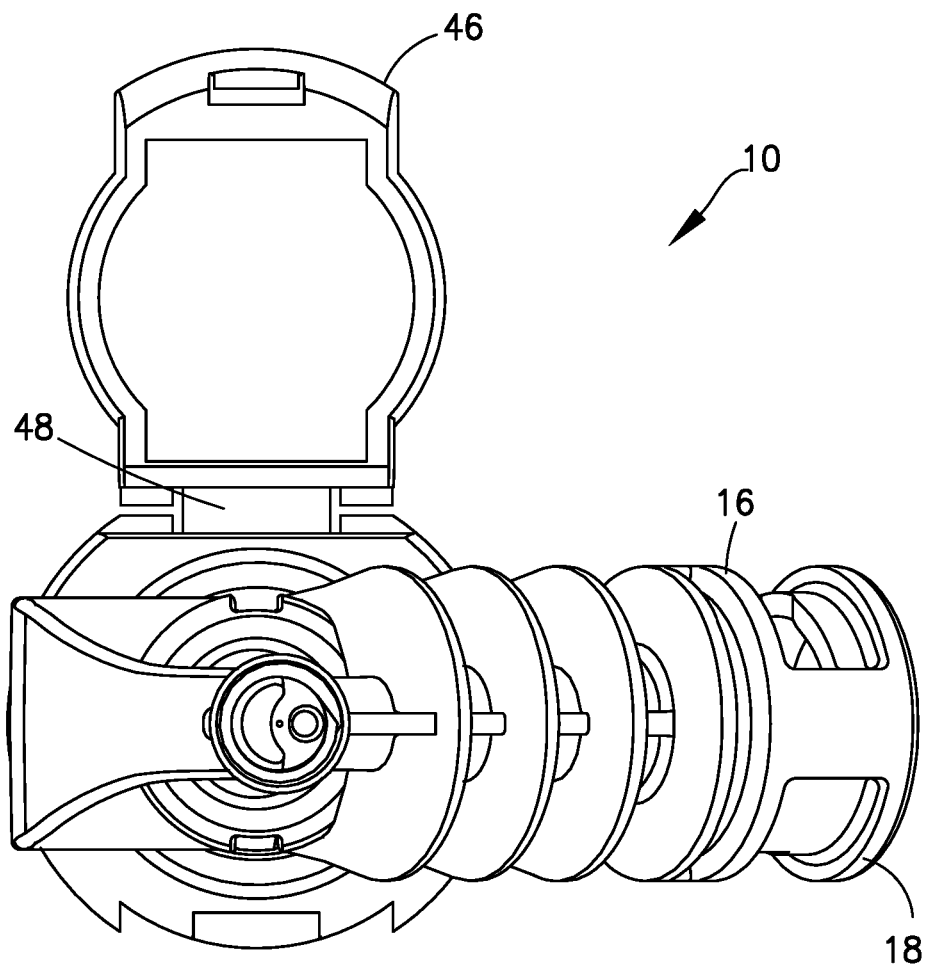
FIG. 10 is a front view of the infusion adapter of FIG. 1 in accordance with an embodiment of the present invention.
Figure 11:
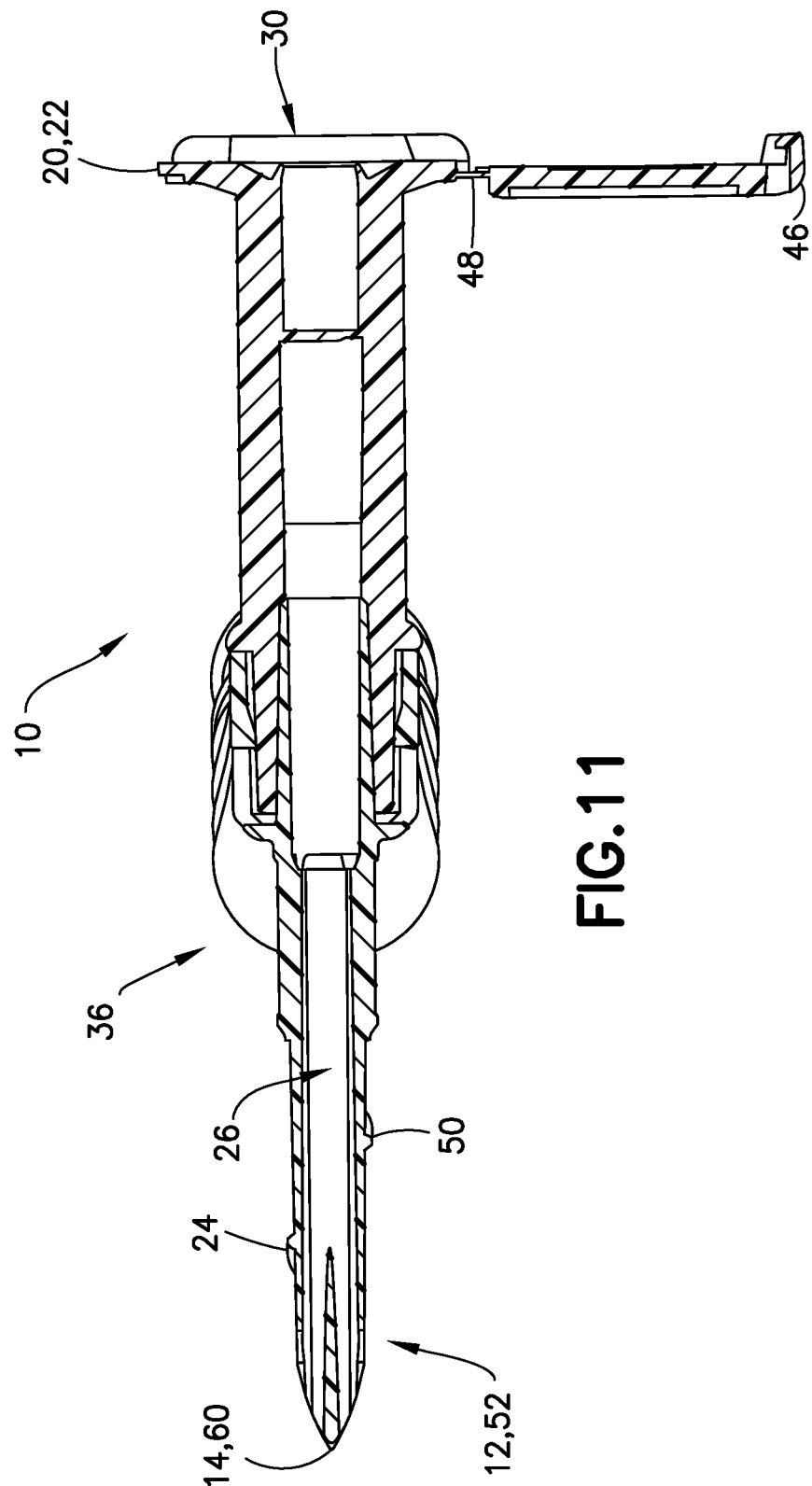
FIG. 11 is a cross-sectional view taken along line 11-11 of the infusion adapter of FIG. 5 in accordance with an embodiment of the present invention.

Referring to FIGS. 3 and 4, in one embodiment, infusion adapter 10 may include an intravenous line connector 34 (FIG. 3) that is removably connectable to a main body 36 (FIG. 4) of infusion adapter 10. In such an embodiment, main body 36 includes an intravenous line connector receiving end 38 having a first connection portion 40 as shown in FIG. 4. Additionally, intravenous line connector 34 includes a main body receiving end 42 having a second connection portion 44 as shown in FIG. 3. Referring to FIG. 3, intravenous line connector 34 includes an end cap 46 that is pivotable via a hinge portion 48 between an open position (FIG. 3) to a closed position.

Intravenous line connector 34 may be connected to main body 36 by positioning main body receiving end 42 of intravenous line connector 34 into engagement with intravenous line connector receiving end 38 of main body 36. In one embodiment, intravenous line connector 34 may be secured to main body 36 by positioning second connection portion 44 of intravenous line connector 34 into engagement with first connection portion 40 of main body 36, and threadingly engaging first connection portion 40 and second connection portion 44. In other embodiments, second connection portion 44 of intravenous line connector 34 may be secured to first connection portion 40 of main body 36 using a press-fit, locking tapers, interference fit, snap-fit, ball detent, locking tabs, spring loaded locking mechanism, latch, adhesive, or other similar mechanism. In this manner, intravenous line connector 34 is locked to main body 36, i.e., significant relative movement between intravenous line connector 34 and main body 36 is prevented. In alternate embodiments, intravenous line connector 34 and main body 36 may be integrally formed.

Referring to FIGS. 1-13, connection portion 12 of infusion adapter 10 includes anchor component 24 and a puncturing point 60 disposed adjacent first end 14. In one embodiment, anchor component 24 includes a helical thread 50 which forms a threaded spike 52. The helical thread 50 extends radially outward from the connection portion 12 and extends about the full length of the connection portion 12. The helical thread 50 has two flank portions and a crest portion that is flat, although any other suitable thread form may be utilized. The starting and ending point of the helical thread 50 may be tapered to form a gradual beginning and end to the helical thread 50. As shown in FIG. 1, the helical thread 50 extends circumferentially once around the connection portion 12 (360 degrees or one revolution), although any other suitable thread pitches may be utilized. Further, although a single helical thread 50 is utilized, the anchor component 24 may include one or more helical threads 50. The helical thread 50 allows for anchor component 24 to engage and interface the interior walls of an injection port 104 when connecting infusion adapter 10 to an infusion fluid container 102. In one embodiment, the thread 50 may self-tap and cut its own thread in the interior walls of injection port 104. In this manner, connection portion 12 of infusion adapter 10 is locked and anchored within injection port 104, i.e., significant relative movement between infusion adapter 10 and injection port 104 of infusion fluid container 102 is prevented and disconnection of infusion adapter 10 from the infusion fluid container 102 is prevented. In an alternative embodiment, threaded spike 52 of connection portion 12 of infusion adapter 10 may threadingly engage corresponding threads located on the interior walls of injection port 104 of infusion fluid container 102.

Figure 12:
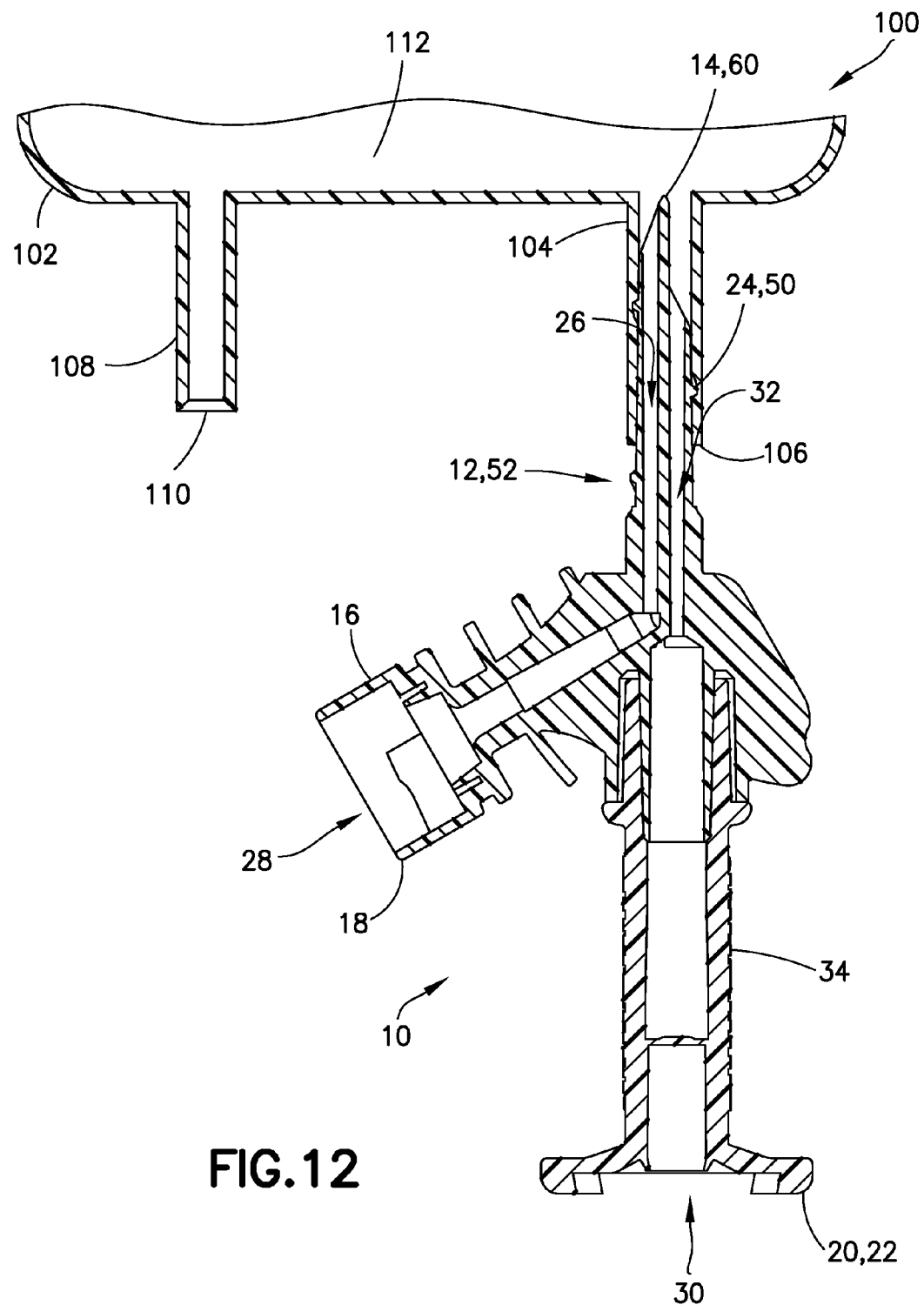
FIG. 12 is a cross-sectional view of the infusion adapter of FIG. 1 with an anchor component of the connection portion of the infusion adapter anchored and securely connected to an injection port of an infusion fluid container in accordance with an embodiment of the present invention.
Figure 13:
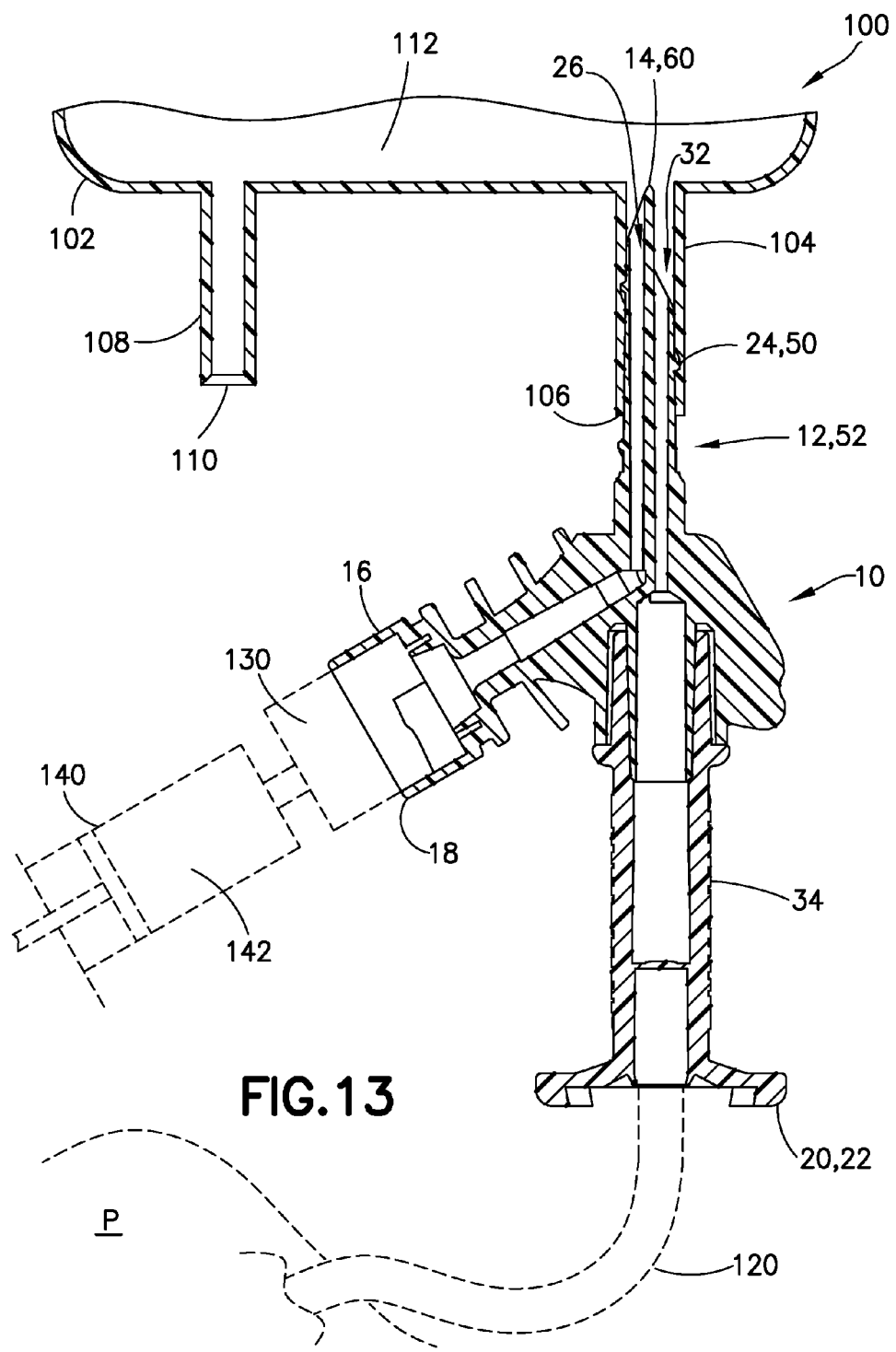
FIG. 13 is a cross-sectional view of the infusion adapter of FIG. 1 with an anchor component of the connection portion of the infusion adapter anchored and securely connected to an injection port of an infusion fluid container, with a syringe assembly containing a medication fluid connected to a first port of the infusion adapter via a connector, and with an intravenous line connected to a second port of the infusion adapter, the intravenous line connected at an opposite end to a bloodstream of a patient in accordance with an embodiment of the present invention.

Referring to FIGS. 12 and 13, anchor component 24 provides a means for connecting first end 14 of infusion adapter 10 to an injection port 104 of an infusion fluid container 102. With the anchor component 24 of connection portion 12 connected to injection port 104 of the infusion fluid container 102, the anchor component 24 securely connects infusion adapter 10 to the infusion fluid container 102 such that disconnection of infusion adapter 10 from the infusion fluid container 102 is prevented. Additionally, anchor component 24 of connection portion 12 anchors infusion adapter 10 to injection port 104 of infusion fluid container 102, i.e., significant relative movement between infusion adapter 10 and injection port 104 of infusion fluid container 102 is prevented. In this manner, anchor component 24 prevents inadvertent and accidental removal of infusion adapter 10 from infusion fluid container 102 and provides a leakproof connection between infusion adapter 10 and infusion fluid container 102 during a drug transfer procedure. Furthermore, anchor component 24 reduces the spiking force required to pierce a fluid barrier member 106 of injection port 104 of the infusion fluid container 102. In particular, the connection portion 12 engages the injection port 104 and is rotated such that the helical thread 50 engages the interior surface of the injection port 104 thereby providing a mechanical advantage to pierce the fluid barrier member 106 and to fully insert the connection portion 12 within the injection port 104. Infusion fluid container 102 may also include a second port 108 and second fluid barrier 110.

In one embodiment, infusion adapter 10 comprises a PhaSeal adapter which is compatible with a Becton Dickinson ("BD") PhaSeal™ System available from Becton, Dickinson and Company of Franklin Lakes, N.J.

As previously discussed, intravenous therapy applications allow patients to receive infusion and medication treatment. For example, therapy may include the administration of medications by IV using intravenous and subcutaneous or hypodermis routes, i.e., into the bloodstream and under the skin. Examples of medical treatments that intravenous therapy applications may provide to a patient include antibiotics, pain management medications, cancer treatments, and similar medications.

Referring to FIG. 13, a patient may be provided with a fluid transfer system 100 that includes intravenous tubing 120 and a connector or injector adapter member 130 that is adapted to receive an injector and/or syringe assembly 140 containing a required medication fluid 142.

When performing infusion, it is often necessary to inject a drug or other medical substance into an infusion fluid 112 located inside an infusion bag or other infusion fluid container 102. This is often done by means of penetrating a septum or fluid barrier member 106 of an injection port 104 on the infusion fluid container 102.

Referring to FIGS. 12 and 13, when a treatment is needed, a patient or a medical practitioner is able to spike or pierce fluid barrier member 106 of injection port 104 of infusion fluid container 102 with puncturing point 60 and anchor component 24 of connection portion 12 of infusion adapter 10. Advantageously, anchor component 24 of infusion adapter 10 in accordance with the present disclosure locks and anchors connection portion 12 of infusion adapter 10 within injection port 104, i.e., significant relative movement between infusion adapter 10 and injection port 104 of infusion fluid container 102 is prevented and disconnection of infusion adapter 10 from the infusion fluid container 102 is prevented as previously discussed.

With infusion adapter 10 securely connected to injection port 104 of infusion fluid container 102 via anchor component 24, a patient or a medical practitioner is able to connect syringe assembly 140 to first port 16 of infusion adapter 10. In one embodiment, a medical practitioner is able to connect syringe assembly 140 to first port 16 of infusion adapter 10 via connector 130 as shown in FIG. 13. Connector 130 could be a piercing member protection connector in accordance with the connector and protection device described in U.S. Pat. No. 8,075,550, filed Jul. 1, 2008, entitled "Piercing Member Protection Device", the entire disclosure of which is hereby expressly incorporated herein by reference.

With syringe assembly 140 connected to first port 16, a medication fluid 142 contained in syringe assembly 140 can be injected into the infusion fluid container 102 via infusion adapter 10. The syringe assembly 140 and connector 130 may then be disconnected from infusion adapter 10 and the infusion fluid container 102 may then be sent to nursing and is ready to be administered to a patient. For example, an intravenous line or intravenous tubing 120 may be connected to second port 20 of infusion adapter 10 as shown in FIG. 13. The other end of the intravenous tubing 120 is connected to a bloodstream of a patient P as shown in FIG. 13. In this manner, a medication may be administered to the patient intravenously.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. An infusion adapter for connection with an infusion fluid container, the infusion adapter comprising:
   a connection portion including an anchor component for connecting to an injection port of the infusion fluid container, the connection portion comprising a spike extending from a proximal end to a puncturing point and the anchor component further comprising at least one protrusion extending radially outward from the spike, and a circumferential path of the at least protrusion extending axially from the proximal end of the spike toward the distal end of the spike;
   a first port adapted for connection with a syringe assembly containing a medication fluid, the first port in fluid communication with the connection portion via a first passageway extending from the first port to a distal opening positioned adjacent to the puncturing point of the spike; and
   a second port adapted for connection with an intravenous line, the second port in fluid communication with the connection portion via a second passageway extending from the second port to a distal opening, the distal opening of the second passageway axially spaced from the distal opening of the first passageway,
   wherein the distal openings of the first passageway and the second passageway are radially opposed at the distal end of the spike, and
   wherein the at least one protrusion of the spike is configured to interfere with the injection port of the infusion fluid container to substantially prevent disconnection of the infusion adapter from the infusion fluid container once the infusion adapter is connected to the infusion fluid container.

2. The infusion adapter of claim 1, wherein the at least one protrusion only extends one revolution circumferentially around the connection portion.

3. The infusion adapter of claim 1, wherein the anchor component reduces a force required by a user to pierce a fluid barrier member of the injection port of the infusion fluid container.

4. The infusion adapter of claim 1, wherein the at least one protrusion is configured to self-tap a corresponding pathway within an internal diameter of the injection port when the spike is inserted into the injection port.

5. An adapter for connection with a container, the adapter comprising:
   a connection portion configured to be connected to a first container, the connection portion including a radial protrusion; and
   at least one port adapted to be connected to a second container, the connection portion configured to be in fluid communication with the at least one port,
   wherein the connection portion and the radial protrusion are configured to be received by a portion of the first container with the protrusion configured to securely connect the connection portion to the first container once the connection portion is connected to the first container, wherein the radial protrusion extends both radially and axially along a circumference of the connection portion, and wherein the radial protrusion only extends one revolution circumferentially around the connection portion, and
   wherein the radial protrusion is configured to deform an internal diameter within at least a portion of the first container when the connection portion is received by the first container.

6. The adapter of claim 5, wherein the radial protrusion reduces a force required by a user to pierce a fluid barrier member of the first container.

7. The adapter of claim 5, wherein the at least one port comprises first and second ports, the first port configured to be connected with the second container, the second port configured to be connected with a third container.

8. The adapter of claim 7, wherein the connection portion defines first and second fluid channels, the first channel in fluid communication with the first port, the second channel in fluid communication with the second port.

9. The adapter of claim 5, wherein the connection portion comprises a spike having a puncturing point.

* * * * *